United States Patent
Harney (10) Patent No.: US 6,277,632 B1
(45) Date of Patent: *Aug. 21, 2001

(54) METHOD AND KITS FOR PREPARING MULTICOMPONENT NUCLEIC ACID CONSTRUCTS

(75) Inventor: Peter D. Harney, Aliso Viejo, CA (US), by Jennifer Harney, executrix (73) Assignee: VectorObjects, LLC, Wellesley, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,034

(22) Filed: Jun. 16, 1997

Related U.S. Application Data (60) Provisional application No. 60/019,869, filed on Jun. 17, 1996.

(51) Int. Cl.$^7$ .................................................. C12N 15/63
(52) U.S. Cl. ..................................... 435/320.1; 435/254.2; 536/24.3; 536/24.5
(58) Field of Search ..................... 435/6, 254.2, 320.1; 536/24.33, 24.3, 24.5

(56) References Cited

U.S. PATENT DOCUMENTS

| | | | |
|---|---|---|---|
| 4,987,073 | 1/1991 | Berman et al. | 435/172.3 |
| 5,128,256 | 7/1992 | Huse et al. | 435/172.3 |
| 5,137,814 | 8/1992 | Rashtchian et al. | 435/91 |
| 5,426,039 | 6/1995 | Wallace et al. | 435/91.2 |
| 5,478,731 | 12/1995 | Short . | |
| 5,962,255 | * 10/1999 | Griffiths et al. | 435/69.1 |

OTHER PUBLICATIONS

Murray, A.W. et al. (1983) "Construction of artificial chromosomes in yeast" *Macmillan Journals Ltd.* 189–194.

Aslanidis C. and de Jong P.J. (1990) "Ligation–independent cloning of PCR products (LIC–PCR)", *Nucleic Acids Research* 18(20):6069–6074.

Brosius J. (1989) "Laboratory Methods Superpolylinkers in Cloning and Expression Vectors", *DNA* 8(10):759–777.

Clark J.M. (1988) "Novel non–templated nucleotide addition reactions catalyzed by procaryotic and eucaryotic DNA polymerases", Laboratory of Molecular Genetics, National Institute of Environmental Health Sciences, Research Triangle Park, NC *Nucleic Acid Research* 16(20):9677–9685.

Marchuk D. et al. (1990) "Construction of T–vectors, a rapid and general system for direct cloning of unmodified PCR products", *Nucleic Acids Research* 19(5):1154.

McNeil D.J. et al. (1992) "Analysis of *Streptomyces avermitilis* genes required for avermectin biosynthesis utilizing a novel integration vetor", *Gene* 111:61–68.

Scharf S.J., et al. (1986) "Direct Cloning and Sequence Analysis of Enzymatically Amplified Genomic Sequences", *Science* 233(4768):1076–1078.

Belev, T.N. et al. (1991) "A Fully Modular Vector System for the Optimization of Gene in *Escherichia coli* " *Plasmid* 2:147–150.

Denis, F. and Brzezinski, R. (1992) "A versatile shuttle consmid vector for use in *Escherichia coli* and actinomycetes" *Genes* 111:115–118.

Gibson, T. et al. (1987) "Lorist6, a Cosmid vector with BamHI, NotI, ScaI and HindIII cloning sites and altered neomycin phosphotransferase gene expression" *Gene* 53:283–286.

Goeddel, D. et al. (1992) "Gene Expression Technology" *Method in Enzymology* 185:512–527.

Watson, J.D. et al. (1994) "Recombinant DNA, Second Edition". pp. 206–209.

Stratagene Catalog, p. 39, 1988.*

Goodchild, Bioconjugate Chemistry 1(3):165–87, May 1990.*

* cited by examiner

*Primary Examiner*—Scott W. Houtteman
(74) *Attorney, Agent, or Firm*—Foley, Hoag & Eliot, LLP; Matthew P. Vincent; James T. Olesen (57) ABSTRACT

The invention provides a highly efficient, rapid, and cost effective method of linking nucleic acid components in a predetermined order to produce a nucleic acid multicomponent construct. The invention further provides nucleic acid components, each nucleic acid component comprising a double stranded nucleic acid molecule having at least one single stranded 5' or 3' terminal sequence, the terminal sequence having sufficient complementarity to either a terminal sequence in a separate nucleic acid component or to a sequence in a linking nucleic acid molecule so as to allow for specific annealing of complementary sequences and linkage of the components in a predetermined order. Kits containing reagents required to practice the method of the invention are also provided.

17 Claims, 2 Drawing Sheets

METHOD AND KITS FOR PREPARING MULTICOMPONENT NUCLEIC ACID CONSTRUCTS

RELATED APPLICATIONS

This application claims the benefit of a previously filed Provisional application No. 60/019,869 filed Jun. 17, 1996, which is hereby incorporated by reference.

BACKGROUND OF THE INVENTION

The essence of recombinant DNA technology is the joining of two or more separate segments of DNA to generate a single DNA molecule that is capable of autonomous replication in a given host. The simplest constructions of hybrid DNA molecules involve the cloning of a DNA sequence of interest (DNA insert) into a pre-assembled cloning vector. The cloning vector includes all of the necessary components for replication of the DNA insert in a compatible host cell, e.g., promoter sequence, origin of replication sequence, termination sequence, and a selectable marker sequence. The DNA insert sequences can be derived from essentially any organism, and they may be isolated directly from the genome, from mRNA, or from previously cloned DNA sequences. Alternatively, the DNA insert sequences can be created synthetically.

Insertion of the DNA sequence of interest can be accomplished by a number of techniques. The most common technique involves restriction enzymes. A restriction enzyme recognition site that is present in both the DNA insert and the vector of interest is cleaved with a restriction enzyme to provide for appropriate termini, the termini of either the DNA insert or the vector are treated with alkaline phosphatase to remove terminal phosphates and avoid undesirable joining, and the DNA sequence of interest is inserted into the vector at the compatible sites during a ligation reaction. A restriction enzyme site present in a pre-assembled vector must be compatible with a restriction enzyme site in the DNA sequence of interest.

Alternatively, the DNA of interest can be modified to obtain compatible restriction sites by filling in of cohesive ends as appropriate, or by the ligation of an appropriate oligonucleotide linker, which can be subsequently cleaved by the restriction enzyme of interest.

Conventional cloning methods can be time consuming and often involve multiple sub cloning steps. Therefore, a need exists for developing a simple and rapid method for synthesizing and identifying an optimal construct for use in a particular application.

SUMMARY OF THE INVENTION

This invention pertains to methods for preparing multicomponent nucleic acid constructs. The invention provides a method of linking nucleic acid components in a predetermined order to produce a nucleic acid multicomponent construct, comprising:

(a) providing the nucleic acid components and optionally a linking nucleic acid molecule to be assembled into the construct, each nucleic acid component comprising a double stranded nucleic acid molecule having at least one single stranded 5' or 3' terminal sequence, the terminal sequence having sufficient complementarity to either a terminal sequence in a separate nucleic acid component or to a sequence in a linking nucleic acid molecule so as to allow for specific annealing of complementary sequences and linkage of the components in a predetermined order;

(b) incubating the nucleic acid components under conditions which allow for the specific annealing and linkage of the nucleic acid components to thereby produce the nucleic acid multicomponent construct.

In a preferred embodiment of the method, the nucleic acid components are flanked by single stranded terminal sequences and these terminal sequences are preferably non-palindromic. The nucleic acid components can be linked either directly via annealing of 5' or 3' complementary terminal sequences or indirectly via a linking nucleic acid molecule (e.g. an oligonucleotide or an adaptor molecule).

The nucleic acid components can be linked either simultaneously or sequentially to form the nucleic acid construct. Sequential assembly is suitable for automation. The method can be used to produce nucleic-acid constructs which are functional as assembled or constructs which are used as subcomponents for the assembly of functional constructs.

The method of the invention can be used to synthesize a group of nucleic acid constructs in which one or more of the components can be substituted, in each of the constructs, with a different nucleic acid component, having the same functionality or characteristic utility. This allows for comparison of the different components and production of an optimal construct for a particular application. Toward this end, the nucleic acid components are designed and synthesized in such a way that a group of nucleic acid components belonging in the same category (i.e., having the same functionality or characteristic utility, e.g. a set of nucleic acid components encoding different promoters) possess the same terminal sequences, such that the same category nucleic acid components can be used interchangeably to assemble a nucleic acid multicomponent construct.

The nucleic acid components may also be covalently or non-covalently modified prior to or following assembly of the nucleic acid multicomponent construct. This allows for the synthesis of constructs having biological properties which cannot be obtained easily using current recombinant methods.

The method of this invention is particularly suitable for the construction of nucleic acid vectors. These include plasmid, viral, or phage vectors, or yeast artificial chromosomes. The vector can be a cloning or expression vector and can be used for the expression of cDNA or genomic libraries, genes or gene fragments, mutagenized genes, recombined fusion genes, and artificial genes. The constructs can be employed in prokaryotic, eukaryotic (mammalian or non-mammalian) expression, construction of unique cDNA libraries, protein, antibody and peptide phage display libraries. The constructs can further be employed in gene transfer, gene therapy, and the creation of transgenic organisms.

According to the method, the vector is assembled from nucleic acid components encoding a single functionality or multiple functionalities. At a minimum, nucleic acid components encoding an origin of replication, a selectable marker and an insert of interest are used. Depending on the type of vector desired, nucleic acid components encoding other vector functions may also be incorporated (e.g. a promoter, a transcription or translation regulatory element, etc.). An expression vector can be produced using a nucleic acid component encoding a structural gene or gene fragment of interest and additional nucleic acid components encoding regulatory elements required for expression of the gene. For example, a cDNA library expression vector is produced using nucleic acid components encoding a collection of cDNA molecules derived from poly(A)+mRNA. Importantly, the optimization procedure of interchanging nucleic acid components described above can be used to create an optimal vector for a particular application.

The reagents required to practice the method of the invention may be provided in the form of a kit. A kit would comprise, in separate containers, the nucleic acid components to be assembled into a construct, and optionally linking nucleic acid molecules as well as buffers, enzymes and an instructional brochure explaining how to use the kit. In a preferred embodiment the kit would provide the nucleic acid components in an appropriately phosphorylated form for ligation.

The invention further provides a kit for the production of vectors. The kit for the production of vectors would minimally comprise nucleic acid components encoding origins of replication, selectable markers and inserts of interest. The kit could also include nucleic acid components encoding other vector functions (e.g. a promoter, a transcription or translation regulatory element, etc.).

The method of the invention is a highly efficient, rapid, cost effective alternative to current recombinant cloning methods in that it enables users to choose from a broad array of different nucleic acid components or modified nucleic acid components when assembling any construct. The method of the invention allows the rapid construction of customized constructs without the need to use restriction enzymes.

Other features and advantages of the invention will be apparent from the following detailed description, and from the claims.

BRIEF DESCRIPTION OF THE DRAWINGS

FIG. 2 shows representative ways of linking nucleic acid components via specific terminal sequences to prepare nucleic acid constructs according to the method of the invention.

DETAILED DESCRIPTION

In order that the invention may be more readily understood, certain terms are first defined.

As used herein, the term "nucleic acid component" describes the basic unit of assembly used in the present invention. Nucleic acid components are comprised of double stranded nucleic acid molecules which contain at their termini specific terminal sequences required for assembling the nucleic acid components into a specific nucleic acid multicomponent construct. The nucleic acid sequences contained within each nucleic acid component provide the requisite information for a specific biological function or for a specific utility deemed essential by the user. Examples of nucleic acid components include the nucleic acid sequences which encode a gene, an origin of replication, or a selection marker.

The term "nucleic acid" refers to polynucleotides such as deoxyribonucleic acid (DNA), and, where appropriate, ribonucleic acid (RNA). The term should also be understood to include, as equivalents, analogs of either RNA or DNA.

As used herein, the term "terminal sequence" is used to describe the terminal single stranded nucleotide sequence of a nucleic acid component. Nucleic acid components having complementary terminal sequences to either separate nucleic acid components or linking molecules enable users to specify the precise organization and orientation of nucleic acid components upon their assembly into constructs.

The terms "complementary" and "compatible" are used herein interchangeably to describe the capacity of a pair of single-stranded terminal sequences to anneal to each other via base pairing (e.g. A-T or G-C). The terminal sequences should contain nucleotide sequences of sufficient length and sequence complementarity so as to allow efficient annealing to occur.

As used herein, the term "palindromic sequence" describes a sequence of DNA that consists of inverted repeats.

As used herein, the term "linkage" refers to a physical connection between two or more nucleic acid components, catalyzed by an enzyme.

As used herein, the term "genomic library" refers to a set of cloned fragments together representing the entire genome of an organism.

As used herein, the term "category" describes a classification of genes, gene fragments, restriction sites, or genetic elements which may be arranged in a systematic order based on a number of user-defined criteria, including the ability to produce or regulate a similar biological activity. For example, the various different origin of replication nucleotide sequences, may be classified into a specific category.

As used herein, the term "hapten" refers to a small molecule that acts as an antigen when conjugated to a protein.

As used herein, the term "genetic element" describes a sequence of nucleotides, including those which encode a regulatory region, involved in modulating or producing biological activity or responses or which provides a specific signal involved in a molecular mechanism or biological activity. For example, a prokaryotic gene may be comprised of several genetic elements, including a promoter, a protein coding region, a Shine-Delgarno sequence, and translational and transcriptional terminators.

As used herein, the term "functionality" describes the normal, characteristic utility of a construct, gene, gene fragment, or genetic element.

As used herein, the term "handle" is used to describe a chemical or biochemical modification to a nucleotide residue within an oligonucleotide or a nucleic acid component. A handle provides a site for covalent or non-covalent attachment of a biological or chemical molecule(s) to a nucleic acid component.

As used herein, the term "oligonucleotide" refers to a single stranded nucleic acid sequence composed of two or more nucleotides. An oligonucleotide can be derived from natural sources, but it is often chemically synthesized by known methods and then purified. It may be of any length and it may be used as a primer, a probe or a component of a ligation reaction.

As used herein, the term "oligonucleotide bridge" is an oligonucleotide used in a ligation reaction to bridge non complementary 5' and 3' terminal sequences in two separate nucleic acid components.

The present invention pertains to a highly efficient, rapid, and cost effective method of producing multicomponent nucleic acid constructs. The method comprises:

(a) providing the nucleic acid components and optionally a linking nucleic acid molecule to be assembled into the construct, each nucleic acid component comprising a double stranded nucleic acid molecule having at least one single stranded 5' or 3' terminal sequence, the terminal sequence having sufficient complementarity to either a terminal sequence in a separate nucleic acid component or to a sequence in a linking nucleic acid molecule so as to allow for specific annealing of complementary sequences and linkage of the components in a predetermined order;

(b) incubating the nucleic acid components under conditions which allow for the specific annealing and linkage of the nucleic acid components to thereby produce the nucleic acid multicomponent construct.

In a preferred embodiment of the invention, the nucleic acid components are used in an appropriately phosphorylated form for ligation. Typically, the nucleic acid components are incubated at a temperature appropriate to promote denaturation, cooled down to an appropriate temperature, such that efficient annealing of the nucleic acid component terminal sequences occurs, and treated with a ligase enzyme to ligate the nucleic acid components and produce a nucleic acid construct. The formed nucleic acid construct can be transformed into a bacterial host for amplification and subsequent purification.

The method of the present invention entails the use of specially designed nucleic acid components to assemble a nucleic acid construct. The nucleic acid components are double stranded nucleic acid molecules having one or more, preferably two terminal sequences designed to be complementary to the terminal sequences of the nucleic acid component intended to be the adjacent component in the construct. For example, in a construct containing five components in order 1–5 (see FIG. 1), the terminal sequence E of nucleic acid component 1 would be compatible only with the terminal sequence E', of nucleic acid component 2, the terminal sequence D of nucleic acid component 2 with the terminal sequence D' of nucleic acid component 3, the terminal sequence C of nucleic acid component 3 with the terminal sequence C' of nucleic acid component 4 and the like. In a preferred embodiment of the method, the nucleic acid components are flanked by single stranded terminal sequences and these terminal sequences are non-palindromic. The nucleic acid components can be linked either directly via annealing of 5' or 3' complementary terminal sequences or indirectly via a linking nucleic acid molecule, which can be, for example, a) an oligonucleotide bridge having a sequence that is complementary to 5' and 3' terminal sequences in two separate nucleic acid components or (b) an adaptor molecule having terminal sequences that are complementary with 5' or 3' terminal sequences in separate nucleic acid components. Alternatively, the nucleic acid components may be provided in the form of single stranded nucleic acid molecules, which would under the appropriate denaturation and annealing conditions, come together to form a double stranded nucleic acid molecule having at least one single stranded 5' or 3' terminal sequence.

In one embodiment of the method, the nucleic acid components can be linked simultaneously to form the nucleic acid construct. Simultaneous assembly involves the incubation of nucleic acid components required for the assembly of a construct of interest, in the same reaction mixture. In another embodiment of the method, the nucleic acid components can be linked sequentially to form the nucleic acid construct. Sequential assembly is performed in a series of different reaction mixtures. This unique attribute lends itself to the automation of construct assembly. The method of the invention uses, preferably, attachment to a solid support as a starting point in the assembly of a series of nucleic acid components, in a defined order, to form a multicomponent nucleic acid construct. The method can be used to produce nucleic acid, constructs which are functional as assembled (e.g. vectors) or constructs which are used as subcomponents for the assembly of functional constructs (e.g. genes or gene fragments attached to regulatory elements required for the expression of the gene or the gene fragment).

In still another embodiment, the method of the invention can be used to synthesize a group of nucleic acid constructs in which one or more of the components is substituted, in each of the constructs, with a different component, having the same functionality or characteristic utility. In this way the function of the different components can be evaluated and an optimal construct for a particular application identified. For example, as Table I shows, a cloning vector comprised of five different categories of nucleic acid components (e.g. origin of replication, resistance gene, promoter, etc.) might be designed so that users could choose amongst 5 different choices of nucleic acid components within each category. The number of permutations, or possible vector combinations, which are achievable from these 25 components is 3,125. Thus, it can be easily shown that a huge variety of different nucleic acid constructs which potentially address a wide range of highly specific user needs can be synthesized using a very small number of nucleic acid components.

TABLE I

| Number of Different Nucleic Acid | Permutation of Constructs |||||
|---|---|---|---|---|---|
| | No. of Components within a Category |||||
| Component Categories | 1 | 2 | 3 | 4 | 5 |
| 1 | 1 | 2 | 3 | 4 | 5 |
| 2 | 2 | 4 | 9 | 16 | 25 |
| 3 | 3 | 8 | 27 | 64 | 125 |
| 4 | 4 | 16 | 81 | 256 | 625 |
| 5 | 5 | 32 | 243 | 1,024 | 3,125 |

In another embodiment, the nucleic acid components may be covalently or non-covalently modified prior to or following assembly of the nucleic acid multicomponent construct. For instance, sites for the attachment of small biological molecules or macromolecular biological molecules, including proteins or carbohydrates may be added, enabling users to synthesize constructs having altered biological properties.

The method of this invention is particularly suitable for the construction of nucleic acid vectors. These include plasmid, viral, or phage vectors, or yeast artificial chromosomes. The vector can be a cloning or expression vector and can be used for the expression of cDNA or genomic libraries, genes or gene fragments, mutagenized genes, recombined fusion genes, and artificial genes. The constructs can be employed in prokaryotic, eukaryotic (mammalian or non-mammalian) expression, construction of unique cDNA libraries, protein, antibody and peptide phage display libraries. The constructs can further be employed in gene transfer, gene therapy, and the creation of transgenic organisms.

According to the method, the vector is assembled from nucleic acid components encoding a single functionality or multiple functionalities. At a minimum, nucleic acid components encoding an origin of replication, a selectable marker and an insert of interest are used. Depending on the type of vector desired, nucleic acid components encoding other vector functions may also be incorporated (e.g. a promoter, a transcription or translation regulatory element, etc.). An expression vector can be produced using a nucleic acid component encoding a structural gene or gene fragment of interest and additional nucleic acid components encoding regulatory elements required for expression of the gene. For example, a cDNA library expression vector is produced using nucleic acid components encoding a collection of cDNA molecules derived from poly(A)+mRNA. Importantly, the optimization procedure of interchanging nucleic acid components described above can be used to create an optimal vector for a particular application.

General Methods Used in the Practice the Invention

The practice of the present invention will employ, unless otherwise indicated, conventional techniques of recombinant DNA, molecular biology, cell biology, cell culture, transgenic biology, microbiology, and immunology, which are within the skill of the art. Such techniques are described in the literature. See, for example, Molecular Cloning A Laboratory Manual, 2nd Ed., ed. by Sambrook, Fritsch and Maniatis (Cold Spring Harbor Laboratory Press: 1989).

Nucleic Acid Purification

Nucleic acid isolation procedures are performed essentially as described in Maniatis et al. Common nucleic acid isolation procedures involve cell lysis by detergents, protease treatment, and CsCl gradient purification. The latter step can be alternatively performed using commercially available binding matrices in the form of columns (e.g. Qiagen Kit).

Oligonucleotide Synthesis

Oligonucleotide synthesis from the phosphoramidite versions of the nucleosides that DNA and RNA are composed from may be carried out on commercially available solid phase oligonucleotide synthesis machines (Needham-VanDevanter, D. R., et al., Nucleic Acids Res., 12:6159–6168, 1984), or chemically synthesized using the solid phase phosphoramidite triester method described by Beaucage et al., ( Beaucage et al., Tetrahedron Letts. 22, No.20:1859–1862, 1981).

Oligonucleotides are purified prior to use. Purification of oligonucleotides can be performed using reverse phase or anion-exchange HPLC and may also be carried out by denaturing or native polyacrylarnide gel electrophoresis. Following purification, oligonucleotides can be phosphorylated using T4 polynucleotide kinase. As used herein, the term "T4 polynucleotide kinase" refers to the enzyme catalyzing the transfer of the terminal (y) phosphate of ATP to the 5' OH-terminus of a nucleic acid molecule.

Restriction Enzyme Digestion

The procedures concerning the use of restriction enzymes, their nucleotide specificity and the appropriate reaction conditions are known to those skilled in the art and readily available. The amounts of enzyme and DNA, the buffer and ionic concentrations, and the temperature and duration of the reaction will vary depending upon the specific application as described in Maniatis et al.

Ligation

Ligation of single stranded terminal sequences is catalyzed by a ligase. As used herein, the term "ligase" refers to an enzyme that is capable of joining the 3' hydroxyl terminus of one nucleic acid molecule to a 5' phosphate terminus of a second nucleic acid molecule to form a single molecule. Most preferably, the T4 DNA ligase is used.

Ligation is carried out at 12° C. to 16° C. to maintain a balance between annealing of the terminal sequences and activity of the enzyme. An appropriate buffer containing the ATP cofactor required by the ligase, is used. When an enzymatic reaction, such as a ligation, is being conducted, it is preferable to provide the elements required for such a reaction in excess, such that the ability to achieve the desired ligation is not limited by the concentration of the elements.

PCR Amplification

The use of PCR is well known in the art and is described in U.S. Pat. No. 4,683,202, the contents of which are expressly incorporated herein by reference. The technique is described in several general sources, which provide adequate guidance to one of skill in the art, including Maniatis et al. and "PCR Protocols, A Guide to Methods and Applications" (Innis et al. eds.), Academic Press, San Diego, Calif., 1990.

Synthesis of the Nucleic Acid Component Terminal Sequences

Important elements of the method of the invention are terminal sequences, which are required for the efficient assembly of multiple nucleic acid components. The preferred type of terminal sequence is non-palindromic, even though palindromic terminal sequences or a mixture of palindromic and non-palindromic terminal sequences could be used. The benefits of using non-palindromic terminal sequences are that there is no possibility of self-ligation and, in general, the terminal sequences may be designed so that only a single pair of terminal sequences are complementary and will exclusively anneal with each other. The size of the terminal sequences may be varied, but in general, the larger the size of the terminal sequence, the greater the fidelity of annealing specific and complementary terminal sequences within a mixture of numerous other terminal sequences. However, in certain preferred embodiments, the terminal sequences are about 6 to about 20 nucleotides in length, about 6 to about 15 nucleotides in length or about 6 to about 10 nucleotides in length.

Terminal sequences may be either 5' or 3' or both (see FIG. 2). The primary constraint is that a 5' terminal sequence, in general, must anneal with a complementary 5' terminal sequence or an oligonucleotide (or series of oligonucleotides) which provide a complementary 5' terminal sequence. Likewise, a 3' terminal sequence must, in general, anneal with either a complementary 3' terminal sequence or an oligonucleotide (or series of oligonucleotides) which provide a complementary 3' terminal sequence.

Terminal sequences may be synthesized by using a number of different methods including, without limitation, the following:

(1) Adaptors may be ligated to restriction enzyme digested nucleic acid components. These adaptor molecules are composed of synthetic oligonucleotides which are designed to be complementary at one end with a restriction enzyme digested nucleic acid molecule and the other end containing a single stranded terminal sequence, preferably non-palindromic.

(2) Oligonucleotide primers, which contain one or more synthetic uracil residues, may be utilized to PCR-amplify a fragment, followed by uracil DNA glycosylase treatment, resulting in 3' terminal sequences, a method described in U.S. Pat. No. 5,137,814, the contents of which are expressly incorporated herein by reference. "Uracil DNA glycosylase" (UDG), a term of art, refers to an activity which cleaves the glycosidic bond between the base uracil and the sugar deoxyribose, only when the monomeric nucleotide dUTP is incorporated into a DNA molecule, resulting in incorporation of a deoxyuridine moiety (Duncan, B. in The Enzymes 14:565 (1981, ed.: Boyer P.). An enzyme possessing this activity does not act upon free dUTP, free deoxyunridine, or RNA (Duncan, supra). The action of UDG results in the production of an "abasic" site. The enzyme does not, however, cleave the phosphodiester backbone of the nucleic acid component. Most preferably, the phosphodiester backbone at an abasic site may be cleaved through the use of an endonuclease specific for such substrates. A preferred enzyme for this purpose is the *E. coli* enzyme, Endonuclease IV. Most preferably, Endonuclease IV is used in conjunction with UDG to remove dU residues from a nucleic acid component.

(3) 5' terminal sequences may be generated in PCR products by using PCR oligonucleotide primers containing alkane diol derivatives, a method described in U.S. Pat. No. 5,426,039, the contents of which are expressly incorporated herein by reference. These same type of modified primers may be used when using non-PCR amplification methods, resulting in the same type of unique terminal sequences as defined by these primers.

In one embodiment, the resulting nucleic acid components containing the terminal sequences, can be isolated by agarose or acrylamide gel electrophoresis followed by elution of the nucleic acid components from the agarose or acrylamide matrix. The two most common ways of elution are either soaking in an appropriate buffer or electroelution, both described in Maniatis et al. Both methods are effective, but soaking is often the method of choice because it is inexpensive, easy and can be accomplished without monitoring. Kits for the purification of nucleic acids from gel matrices may also be used (e.g. "Compass Kit", American Bioanalytical). In another embodiment, the resulting nucleic acid components, containing the terminal sequences, can be purified using reverse phase or anion-exchange HPLC.

Assembly of the Nucleic Acid Components

In the method of the invention, the various nucleic acid components are designed so that each component contains specific and unique terminal sequences at either end. Each terminal sequence is designed to anneal and base pair with a unique complementary terminal sequence residing on a separate nucleic acid component. A series of specific annealing reactions occur between complementary terminal sequences. This results in the assembly of a larger nucleic acid multicomponent construct having a defined relative order and orientation for all the components.

Figure 2A:
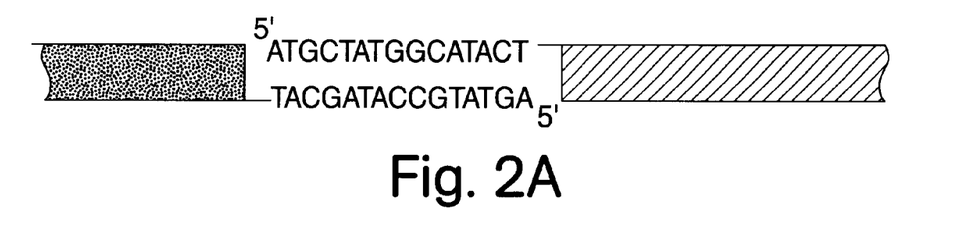
FIG. 2(A) shows annealing of non-palindromic complementary terminal sequences.
Figure 2B:
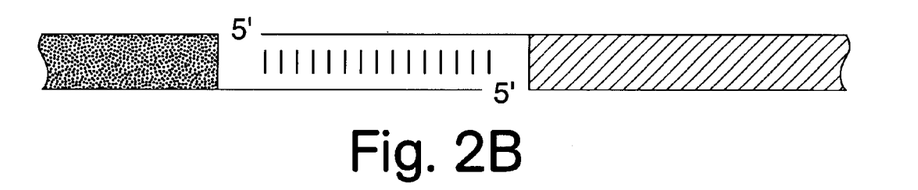
FIG. 2(B) shows annealing of 5' compatible terminal sequences.

According to the method of the invention, the various nucleic acid components can be linked via, without limitation, the following:

(1) Annealing of 5' complementary terminal sequences in two separate nucleic acid components (FIG. 2B).

Figure 2C:
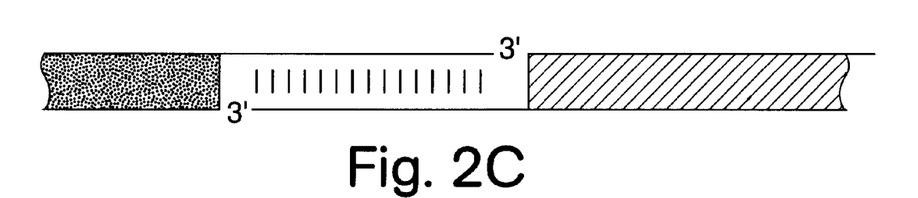
FIG. 2(C) shows annealing of 3' compatible terminal sequences.

(2) Annealing of 3' complementary terminal sequences in two separate nucleic acid components (FIG. 2C).

Figure 2D:
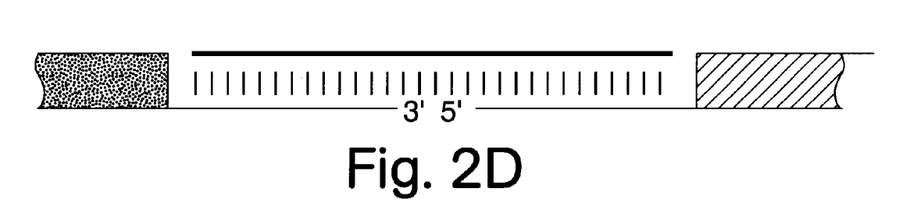
FIG. 2(D) shows linking of non-compatible terminal sequences via an oligonucleotide bridge (thick line)

(3) Annealing of an oligonucleotide bridge with complementary 5' and 3' terminal sequences in two separate nucleic acid components (FIG. 2D).

Figure 2E:
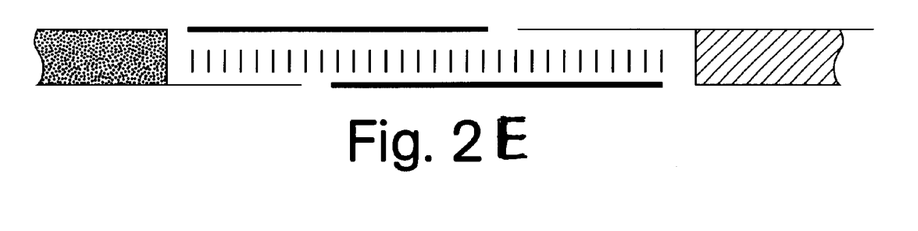
FIG. 2(E) shows linking of non-compatible terminal sequences via an adaptor (thick lines).

(4) Annealing of an adaptor molecule with complementary 5' or 3' terminal sequences in two separate nucleic acid components (FIG. 2E).

The fidelity of assembly of the nucleic acid multicomponent construct depends upon a number of factors, including, without limitation, the following: (1) The number of different nucleic acid components, (2) The size of the terminal sequences, (3) The way anealing occurs, (4) The annealing conditions, (5) The nucleotide sequence within the terminal sequences.

In a preferred embodiment of the invention, three or more nucleic acid components are used for the production of a nucleic acid construct. Preferably three, four, five, or six nucleic acid components are used and more preferably three to eight nucleic acid components are used. Using the method of the invention, the various nucleic acid components can be incubated either simultaneously or in a step-wise fashion, to form nucleic acid multicomponent constructs which can be either functional as assembled or which can be used as subcomponents for the assembly of functional constructs. Three or more nucleic acid components may be linked to form a nucleic acid multicomponent construct. Functional constructs may be assembled from such nucleic acid multicomponent constructs, with each multicomponent construct essentially performing as a single nucleic acid component in the assembly of a functional construct. Nucleic acid multicomponent constructs would be preferably employed when there are a large number of different nucleic acid components requiring assembly, when there are non-unique terminal sequences within a group of different nucleic acid components, or when the size of the final assembled functional construct is very large. Nucleic acid multicomponent constructs may also be used in repetitive cloning experiments or in the design of assembly reactions which are repetitive or otherwise simplified.

Typically, the nucleic acid components would include an appropriately phosphorylated terminal sequence, suitable for ligation to a separate nucleic acid component. The nucleic acid components are incubated under appropriate conditions that allow for efficient annealing of the complementary terminal sequences. Appropriate annealing conditions are described in Maniatis et al. In a particularly preferred embodiment of the invention, the nucleic acid components are incubated in equimolar concentrations, heated to 65° C., and then cooled down slowly to 25° C. Temperatures ranging from 60° to 75° C. may be used depending on the size of the terminal sequences employed.

In certain preferred embodiments of the invention, the nucleic acid components are treated with a ligase enzyme to ligate the nucleic acid components and produce a nucleic acid construct. Preferably a T4 DNA ligase is used, even though the *E. coli* ligase may also be used for certain applications. In another embodiment of the method of the invention, ligation of the different nucleic acid components may not be necessary prior to transferring the assembled nucleic acid construct into the appropriate biological or experimental system.

Preparation of Synthetically or Covalently Modified Nucleic Acid Components

A unique feature of the method of the invention is that, since nucleic acid components may be made synthetically, any nucleic acid component may be altered or modified to contain one or more modifications (i.e., handles). Handles may act as sites of attachment for small biological molecules or macromolecular biological molecules, including proteins or carbohydrates. They may also serve as sites of attachment for chemically synthesized, non-biological molecules. The method of the invention, therefore, enables users to synthesize constructs having altered biological properties.

Modifications which could be performed on nucleic acid components include, without limitation, the following: Modification of nucleic acid residues, biotinylation, fluorescent tagging, incorporation of polypeptide nucleic acids (PNA), covalent or non-covalent conjugation of proteins involved in nucleic acid modification, including enzymes, covalent or non-covalent conjugation of proteins or other components or ions which enable the recognition and binding of specific molecular targets, including haptens.

Modification of nucleic acid residues can be performed by a variety of art known techniques. The simplest method for performing oligonucleotide directed mutagenesis is by enzymatic primer extension (PCR). In this method, an oligonucleotide primer is designed that carries the mutation of interest flanked by 10 to 15 nucleotides of wild-type sequence. This "mutagenic" oligonucleotide can then be used in a PCR reaction along with an oligonucleotide primer containing one or more synthetic uracil residues or alkane diol derivatives to create the nucleic component of interest. The types of mutations that can be made by this approach range from single nucleotide substitutions to deletions or insertions, limited only by the size of the oligonucleotide primer needed.

The synthesis of biotinylated nucleotides is well known in the art and was first described by Langer et al. (PNAS 78:6633–37, 1981). Biotin, a water soluble vitamin, is covalently attached to the C5 position of the pyrimidine ring via an allylamine linker arm. Biotinylation of DNA can be achieved by either nick translation, adapted successfully to incorporate biotinylated nucleotides (biotin-11 and biotin-16-dUTP, biotin-14-dATP), or random-priming using biotinylated octamers. Biotinylated nucleic acid molecules can be prepared from biotin-NHS (N-hydroxy-succinimide) using techniques well known in the art (e.g., biotinylation kit, Pierce Chemicals, Rockford, Ill.).

Fluorescent tagging of nucleic acid molecules can be performed using techniques well known in the art (e.g. using the Fluore-dUTP Labelling Mix by Pharmacia) Examples of suitable fluorescent materials include umbelliferone, fluorescein, fluorescein isothiocyanate, rhodamine, dichlorotriazinylamine fluorescein, dansyl chloride or phycoerythrin.

In an embodiment of the invention, synthetic oligonucleotides are used that contain polypeptide nucleic acids or functional groups like primary amines, sulfhydryls, disulfides, and any other group typically used for conjugation of haptens, proteins, enzymes or antibodies.

Assembly of Vector Constructs

Another aspect of the invention pertains to the assembly of vectors, preferably expression vectors, using a series of interchangeable nucleic acid components. As used herein, the term "vector" refers to a nucleic acid molecule capable of transporting another nucleic acid to which it has been linked. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

One type of vector produced by the method of the invention is a minimal vector (referred to usually as a plasmid vector), which is basically a circular double stranded DNA loop into which additional DNA segments can be ligated. Another type of vector, produced by the method of the invention, is a vector capable of directing the expression of genes to which it is operatively linked. Such a vector is referred to herein as an "expression vector". The invention is intended to include the production of various forms of expression vectors, such as vectors derived from bacteriophage, including all DNA and RNA phage (e.g. cosmids), or viral vectors derived from: (a) all eukaryotic viruses, such as baculoviruses and retroviruses, (b) adenoviruses and adeno-associated viruses, Herpes viruses, Vaccinia viruses and all single-stranded, double stranded and partially double stranded DNA viruses, (c) all positive and negative stranded RNA viruses, and (d) replication defective retroviruses.

Another type of vector produced by the method of the invention is a yeast artificial chromosome (YAC), which contains both a centromere and two telomeres, allowing YACs to replicate as small linear chromosomes. YACs can carry several hundred thousand base pairs of DNA, making them appropriate for genome mapping procedures.

Each nucleic acid component involved in the assembly of a vector construct is intended to encode a specific biological functionality or multiple functionalities. For example, plasmid vectors generally contain several genetic elements such as the following: (a) an origin of replication, (b) a selectable marker element, (c) an insert of interest, for the insertion of genetic elements, such as a specific gene coding for a protein of interest.

The method of the present invention enables nucleic acid components to be synthesized to contain specific and unique terminal sequences such that annealing of complementary terminal sequences between different components will result in the generation of definable and specifically oriented constructs. A vector may be constructed by combining a set of nucleic acid components which provide all the necessary genetic elements required to generate a functional vector, while the unique terminal sequences on each component will determine the order in which all of the nucleic acid components are assembled relative to each other.

Figure 1:
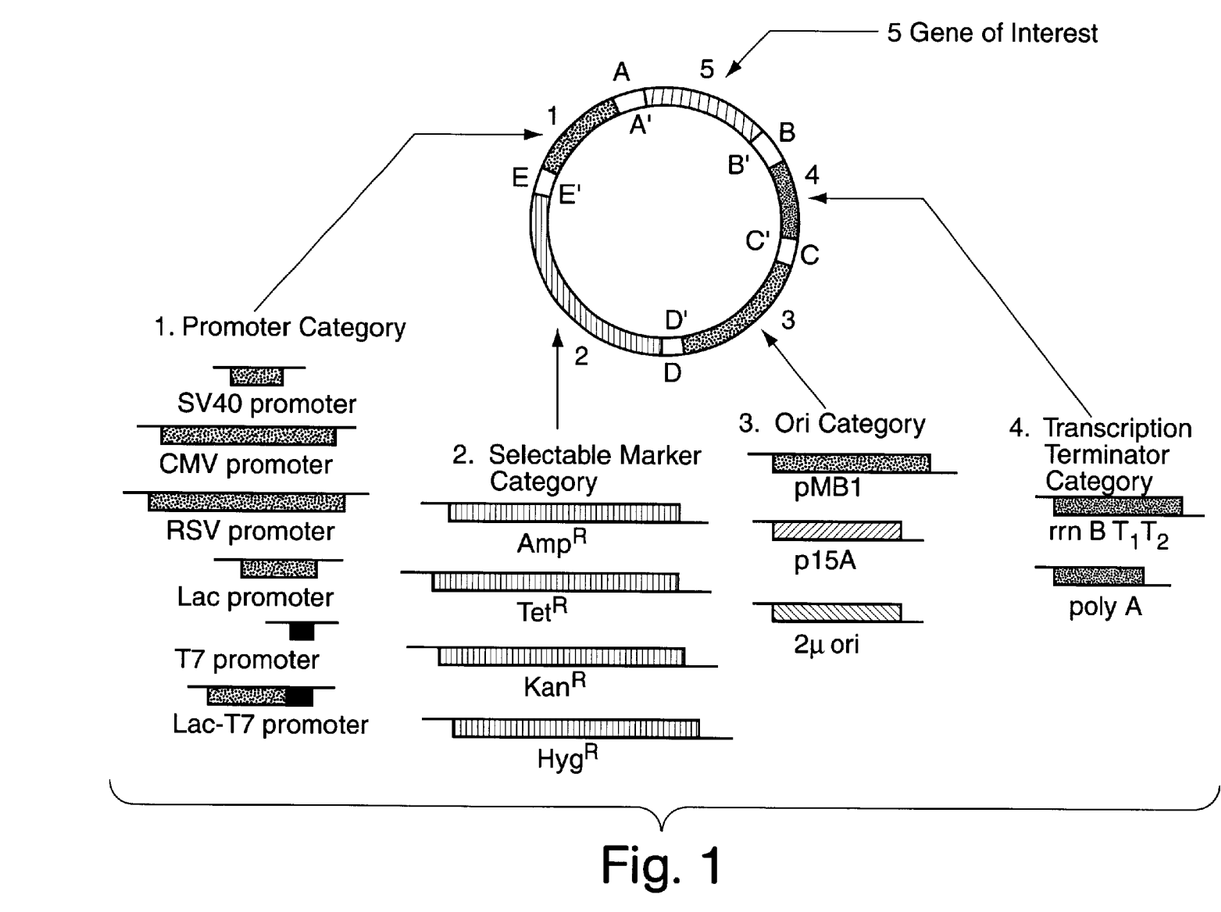
FIG. 1 is a schematic representation of the assembly of a circular plasmid, using the method of the invention. The plasmid vector is assembled by combining a set of nucleic acid components which possess complementary terminal sequences, as well as all of the necessary genetic elements required to generate a functional plasmid construct. A partial list of different interchangeable nucleic acid components and their respective categories is shown, demonstrating the flexibility and utility of the method of the invention.

According to the method of the invention, individual nucleic acid components may be substituted with other components containing the same unique terminal sequences (see FIG. 1). For example, the plasmid origin of replication (ori) is a genetic element of a particular category, whose function is to initiate and regulate plasmid replication in bacteria, provide host range specificity, and regulate plasmid copy number and plasmid compatibility. This general functionality may be provided by a variety of different nucleic acid components within the ori category, including ori segments, ori genes or ori genetic elements. This invention allows for the synthesis and utilization of a series of different ori nucleic acid components, each having the same unique terminal sequences, which would enable users to rapidly and easily choose from a catalog of interchangeable ori nucleic acid components when designing and specifying a plasmid construct. Examples of origins of replication include the pMB1, p15A, 2 $\mu$, ColE1, psc101, F, R6K, R1, RK2, and $\lambda$dv origins of replication.

"Selectable marker" as used herein, refers to the marker and to the nucleic acid encoding said marker. Selectable markers contemplated by the present invention include resistance to antibiotics such as ampicillin, tetracycline, chloramphenicol, kanamycin, neomycin, rifampicin, carnebicillin, streptomycin, and the like. The selectable markers also encompass resistance to drugs such as hygromycin and methotrexate, heavy metals such as cadmium, phage infection, and sensitivity to enzymes which affect calorimetric changes such as β-galactosidase.

A vector may be assembled from multiple individual nucleic acid components, including, without limitation, nucleic acid components which incorporate one or more of the following: (a) origin of replication (bacterial, viral, phage, yeast, mammalian, eukaryotic), (b) selectable markers (antibiotic resistance, drug resistance, mutagenic resistance), (c) promoters (phage, bacterial, yeast, eukaryotic, mammalian), (d) regulatory elements or genes (repressors, enhances), (e) structural genes, (f) fragments of structural genes, (g) translational elements (Shine-Delgarno element, Kozak sequence), (h) terminators of transcription, (i) regulators of mRNA stability (degradation signals, translational regulators), (j) protein encoded elements specifying cellular location (leader sequence, KDEL, CAAX box, nuclear targeting elements), (k) recombination elements (Lox-CRE, M13 ori), (l) mutagenized genes, (m) protein domain encoded regions, (n) synthetic multiple cloning sites, (o) unique restriction enzyme or DNA cleavage sites, (p) site for covalent or non covalent attachment of a biological or chemical molecule (see "Handle").

In a preferred embodiment of the invention, an expression vector is produced. The expression vector produced by the method of the invention comprises nucleic acid components encoding one or more regulatory sequences, selected on the basis of the host cells to be used for expression, as well as the nucleic acid sequence to be expressed. The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors produced by the method of the invention can be introduced into host cells to thereby produce proteins or peptides, including fusion proteins or peptides.

The expression vectors produced by the method of the invention can be, for example, designed for expression of a gene of interest in prokaryotic or eukaryotic cells. For example, the expression vectors can be used for expression in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the expression vectors produced by the method of the invention can be transcribed and translated in vitro, for example using the T7 promoter regulatory sequences and the T7 polymerase. The expression vectors produced by the method of the invention can also be used to produce nonhuman transgenic animals. Furthermore, the nucleic acid vectors produced by the method of the invention can be used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054–3057). Vector constructs assembled using the method of the invention may also be used as templates to synthesize RNA using standard methods. Examples of RNA molecules which could be made, would include, without limitation, the following: mRNA, tRNA, rRNA, snRNA, hnRNA, viral or phage RNA, or modified RNA genes or genetic elements.

Assembly of Genomic and cDNA Libraries

A. Genomic Libraries

One aspect of the present invention pertains to the assembly of genomic libraries from individual nucleic acid components. Using the method of the invention, eukaryotic organism (e.g. viral) or prokaryotic organism (e.g. phage) genomes may be assembled in unique ways. The genome of an organism may be endonucleolytically or exonucleolytically cleaved using suitable restriction enzymes, followed by ligation of specific adaptor molecules, as described above.

For example, in one embodiment, the Lambda phage genome which is an approximately 50 kb double stranded DNA molecule encoding multiple genetic regulatory elements as well as approximately 30–40 structural genes, can be provided in the form of nucleic acid components. Toward this end, each of the Lambda phage genes, or groups of genes can be synthesized to contain unique terminal sequences so that these genes, or groups of genes may be rapidly and efficiently assembled in a specific order and orientation relative to each other.

In still another embodiment of the method of the invention, partial or complete eukaryotic or prokaryotic genomes may be both assembled and modified simultaneously. The method of the invention enables users to alter or mutagenize one or more of the genes or gene fragments, resulting in the creation of genetic alterations such as a mutated gene, a gene deletion, an enhanced gene function, a fusion gene, an altered regulation of the gene functionality, an addition or deletion of restriction enzyme sites or an addition of a site for covalent or non-covalent attachment of a biological or chemical molecule ("handle").

Viral genomic libraries can be created, for example, for the following viruses: (a) all bacteriophage, including all DNA and RNA phage, (b) all eukaryotic viruses, such as baculoviruses and retroviruses, (c) adenoviruses and adeno-associated viruses, Herpes viruses, Vaccinia viruses and all single-stranded, double stranded and partially double stranded DNA viruses, (c) all positive and negative stranded RNA viruses, and (d) replication defective retroviruses.

B. Assembly of CDNA libraries

Another aspect of the present invention pertains to the assembly of cDNA libraries from individual nucleic acid components. Genes or gene fragments derived from mRNA may be assembled in a manner similar to the above, by synthesizing the resulting cDNA molecules so that they contain unique, and in general, non-palindromic terminal sequences. Such cDNA molecules may then be assembled into eukaryotic or prokaryotic expression vectors. This would allow users to choose from a variety of nucleic acid components derived from cDNA and rapidly and flexibly assemble cDNA libraries . Conventional molecular methods could then be used to select or screen these libraries for the clone or clones of interest In the method of the invention, cDNA would be made from mRNA according to art known techniques, described in Maniatis et al., using slight modifications. The method of the present invention uses modified oligonucleotide primers, containing uracil or alkane diol derivatives as described above, to synthesize a first strand of cDNA resulting in the formation of a unique terminal sequence at the 3' end of the gene. An engineered adaptor, as described above, may be then ligated to the 5' end of a double stranded cDNA molecule, resulting in a unique terminal sequence at the other end of the molecule. The resulting nucleic acid components, encoding the various cDNA molecules, would then be used along with other nucleic acid components encoding appropriate genetic elements, to assemble cDNA library expression vectors.

Solid Phase Synthesis

In one embodiment of the method, the nucleic acid components can be linked sequentially to form the nucleic acid construct. This unique attribute lends itself to the automation of construct assembly. The method of the invention uses, preferably, attachment to a solid support as a starting point in the assembly of a series of nucleic acid components, in a defined order, to form a multicomponent nucleic acid construct.

For example, the initial nucleic acid component is attached to a solid support by methods known in the art. Additional nucleic acid components, designed to contain unique terminal sequences at either end, are added in a step-wise fashion, as single components or non-functional multicomponent constructs, and the assembly of components is based on the specific annealing of complementary terminal sequence pairs as previously described. Nucleic acid components may be ligated together, using a ligase enzyme, after each nucleic acid component addition step in the assembly of the larger construct. Unligated DNA fragments may be removed by washing the solid support. Following synthesis, the assembled multicomponent construct or functional construct may be subsequently cleaved from the solid support.

Examples of solid supports that can be used, for the attachment of the initial nucleic acid component, include cellulose, synthetic polymeric material such as modified polystyrenes or polydimethyl acrylamides, and controlled-pore glass. The assembled nucleic acid construct may be cleaved from the solid support by, for example, ammonium hydroxide treatment. Alternatively, the initial nucleic acid component attached to the solid support could be designed to contain a unique restriction site that would be cleaved upon treatment with the appropriate enzyme to release the assembled to nucleic acid construct in solution.

Kits

The reagents required to practice the method of the invention may be provided in the form of a kit. A kit would comprise, in separate containers, the nucleic acid components to be assembled into a construct, and optionally linking nucleic acid molecules as well as buffers, enzymes and an instructional brochure explaining how to use the kit. In a preferred embodiment the kit would provide the nucleic acid components in an appropriately phosphorylated form for ligation.

The invention further provides a kit for the production of vectors. The kit for the production of vectors would minimally comprise nucleic acid components encoding origins of replication, selectable markers and inserts of interest. The kit could also include nucleic acid components encoding other vector functions (e.g. a promoter, a transcription or translation regulatory element, etc.).

Applications Employing the Constructs of the Invention

The nucleic acid constructs produced by the method of the invention, can be employed in an application selected from the group consisting of prokaryotic, eukaryotic (mammalian or non-mammalian) expression. For example, the expression vectors can be used for expression in bacterial cells such as *E. coli*, insect cells (using baculovirus expression vectors) yeast cells or mammalian cells or they can be transcribed and translated in vitro, for example using the T7 promoter regulatory sequences and the T7 polymerase. Alternatively, the nucleic acid constructs can be employed in the construction of unique cDNA libraries, protein, antibody and peptide phage display libraries. Kits for screening phage display libraries are commercially available (e.g., the Stratagene SurfZAP™ Phage Display Kit, Catalog No. 240612). The constructs can further be employed in gene transfer, gene therapy, and the creation of transgenic organisms, as described above. Finally, vector constructs assembled using the method of the invention may also be used as templates to synthesize RNA using standard methods. Examples of RNA molecules which could be made, would include, without limitation, the following: MRNA, tRNA, rRNA, snRNA, hnRNA, viral or phage RNA, or modified RNA genes or genetic elements.

EXAMPLES

The following examples are by way of illustration and are not intended to limit the claims. Persons of skill will readily recognize that the protocols of the examples can be modified in numerous non-critical ways.

Example 1

Simultaneous assembly of a viable plasmid vector

To demonstrate the simultaneous assembly of multiple nucleic acid components having unique, non-palindromic terminal sequences, to produce a viable plasmid vector, three nucleic acid components are used. The first nucleic acid component is a gene coding for green fluorescent protein, 0.7 Kb in length, the second one is a 0.6 Kb molecule coding for terminator sequences and a histidine tag, and the third one is a 2.5 Kb molecule coding for the lac promoter, an ampicillin resistance gene, and an origin of replication.
1. Synthesis of the Nucleic Acid Components The nucleic acid components used in the present example are synthesized by PCR amplification. The PCR reactions are performed in varying volumes (in general, 10–100 microliters) containing a 50 mM KC1, 10 mM Tris-HCI (pH 8.4), 1.5 mM $MgCl_2$ buffer and 0.2 mM of each dNTP, 1.25 units of taq DNA polymerase, $10^{-5}$ M template molecules, and 20 pmol of each primer. The primers used contain uracil residues at specific locations in order to generate 3' terminal sequences as described in U.S. Pat. No. 5,137,814. The PCR reaction is carried out using a thermal cycling instrument, where there is an initial denaturation phase of 95° C. for 5 minutes, followed by multiple cycles (20–40 cycles) of a denaturation step at 94° C., an annealing step at 37°–65° C. and an extension step at 72° C. The resulting PCR products are analyzed by gel electrophoresis to determine size and purity.
2. Generation of Terminal sequences Following PCR amplification and purification of the correct size fragments, the PCR products (approximately 100–200 ng) are dissolved in 10 microliters of the UDG reaction buffer (25 mM Tris-HCI (pH 7.8), 10 mM $Mg_2Cl$, 4 mM beta-mercaptoethanol, 0.4 mM ATP). Single-stranded 3' Terminal sequences are made by treatment of the PCR product with 1–2 units of uracil DNA glycosidase (UDG) for 10 minutes at 37° C. The enzyme is inactivated and reaction is terminated by heating the sample at 65° C. for 10 minutes.

3. Assembly and Ligation of the Nucleic Acid Components

To assemble the vector the individual purified nucleic acid components are mixed in equimolar amounts (approximately 20–200 ng total in 20 microliters) in the UDG treatment buffer and heated to 65° C., followed by gradually cooling down to room temperature (25° C.), to permit efficient annealing of the complementary ends of the nucleic acid components. The reaction mixture may optionally be treated with T4 DNA ligase at 14° C. overnight to ligate the nucleic acid components or used directly to transform competent bacterial hosts.

4. Transformation

A 10 μl aliquot of the assembled vector is added to 100 μl of competent E. coli cells (DH5α), transformed following the manufacturers recommendations, and plated on LB plates containing ampicillin and IPTG.

5. Analysis of the Vector Construct

Isolated fluorescent colonies are selected and pure DNA plasmid prepared using a mini-prep. Correct assembly of the vector construct is determined using standard molecular biological methods, such as restriction enzyme digestion and agarose gel electrophoresis.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A kit for the production of nucleic acid multicomponent constructs, comprising a package containing at least three nucleic acid components, including a first nucleic acid component selected from a category of first nucleic acid components having a common biological utility or functionality, a second nucleic acid component selected from a category of second nucleic acid components having a common biological utility or functionality, and a third nucleic acid component selected from a category of third nucleic acid components having a common biological utility or functionality and, optionally, at least one oligonucleotide bridge, wherein the biological utility or functionality of each of the first, second and third categories is different from the other categories, wherein at least two of the at least three nucleic acid components are supplied as a library of two or more different nucleic acid fragments, and wherein each of the first, second, and third nucleic acid components comprises a double stranded nucleic acid molecule having at least one unique non-palindromic single stranded 5' or 3' terminal sequence, which allows for specific annealing and linkage of the first, second, and third nucleic acid component, and optionally the at least one oligonucleotide bridge, in a predetermined order.

2. The kit of claim 1, wherein each of the first, second, and third nucleic acid components is appropriately phosphorylated for ligation.

3. A kit for the production of vectors, comprising a package containing at least three nucleic acid components, including an origin of replication, a selectable marker, and an insert of interest, and, optionally, at least one oligonucleotide bridge, wherein at least two of the at least three nucleic acid components are supplied as a library of two or more different nucleic acid fragments, and wherein each of the origin of replication, the selectable marker, and the insert of interest comprises a double standard nucleic acid molecule having at least one unique non-palindromic single stranded 5' or 3' terminal sequence, which allows for specific annealing and linkage of the origin of replication, the selectable marker, and the insert of interest, and optionally the at least one oligonucleotide bridge, in a predetermined order.

4. A method of obtaining one or more species of a nucleic acid construct optimal for a particular application comprising:

(a) providing at least three nucleic acid components, including (i) a first component comprising a library of two or more different nucleic acid fragments, each supplying a specific biological utility or functionality chosen from a first category of biological utilities or functionalities, (ii) a second component comprising a library of two or more different nucleic acid fragments, each supplying a specific biological utility or functionality chosen from a second category of biological utilities or functionalities, and (iii) a third component comprising one or more third nucleic acid fragments, each supplying a specific biological utility or functionality chosen from a third category of biological utilities or functionalities, wherein said nucleic acid fragments are double stranded nucleic acid molecules having at least one unique nonpalindromic single stranded 5' or 3' terminal sequence which facilitates specific annealing and linkage of said nucleic acid fragments in a specific order; and wherein the biological functionality or utility of each of the first, second, and third categories is different from that of the other categories, (b) contacting said first, second and third nucleic acid components so that said nucleic acid fragments become specifically annealed and linked so as to produce a library of at least 4 different vector sequences from which one or more species optimal for a particular application may be obtained, and (c) isolating one or more species optimal for a particular application.

5. A method for generating a library of vectors, comprising (i) providing at least 3 different types of nucleic acid components, each representing a functionality to be included in a vector, wherein (a) at least two of said nucleic acid components types are provided as a library of two or more different nucleic acids, and (b) said nucleic acid components are double-stranded nucleic acid molecules having at least one unique non-palindromic single stranded 5' or 3' terminal sequence which facilitates specific annealing and linkage of said components; and (ii) annealing and ligating said nucleic acid components to generate a library of at least 4 different vector sequences.

6. The method of claim 4 or 5, wherein a library of at least 27 different vector sequences is generated.

7. The method of claim 6, wherein a library of at least 625 different vector sequences is generated.

8. The method of claim 7, wherein a library of at least 1024 different vector sequences is generated.

9. The method of claim 4 or 5, wherein said specific biological utility or functionality is selected from the group consisting of: an origin of replication, a selectable marker gene, a protein coding region, a transcription regulatory element, and a translation regulatory element.

10. The method of claim 9, wherein the origin of replication is selected from the group consisting of: a bacterial origin of replication, a viral origin of origin of replication, a phage origin of replication, a eukaryotic origin or replication, a yeast origin of replication, and a mammalian origin of replication.

11. The method of claim 9, wherein the selectable marker gene is selected from the group consisting of: an antibiotic resistance selectable marker, a drug resistance selectable marker, and a mutagenic resistance selectable marker.

12. The method of claim 5, wherein the library of vectors is selected from the group consisting of a library of DNA virus vectors, a library of RNA virus vectors, a library of single-stranded virus vectors, a library of double-stranded virus vectors, a library of baculovirus vectors, a library of retrovirus vectors, a library of adenovirus vectors, a library of adeno-associated virus vectors, a library of Herpes virus vectors, a library of Vaccinia virus vectors, a library of replication defective retrovirus vectors, and a library of artificial chromosome vectors.

13. The method of claim 4, wherein the one or more optimal species isolated is optimized for a function selected from the group consisting of: optimal expression, optimal gene transfer activity, and optimal gene therapy activity.

14. The kit of claim 1, wherein at least two of said at least three nucleic acid components are supplied as at least three different nucleic acid species, each of which provides an alternative form of the common biological utility or functionality of the nucleic acid component.

15. The kit of claim 1, wherein the common biological utility or functionality is selected from the group consisting of: an origin of replication, a selectable marker, a promoter, a regulatory element, a translational element, a transcriptional terminator, a sequence which regulates mRNA stability, a subcellular localization element, a recombinational element, a synthetic multiple cloning site, a unique restriction enzyme or DNA cleavage site, a site for the covalent or noncovalent attachment of a biological or chemical molecule, and a protein coding sequence.

16. The kit of claim 15, wherein the regulatory element is selected from the group consisting of: a promoter, and enhancer, a polyadenylation signal.

17. The kit of claim 15, wherein the protein coding sequence is selected from the group consisting of: a cDNA, a structural gene, a fragment of a structural gene, a mutagenized structural gene, and a mutagenized fragment of a structural gene.

* * * * *